United States Patent
McDaniel

(10) Patent No.: US 10,143,639 B2
(45) Date of Patent: Dec. 4, 2018

(54) USE OF ADELMIDROL AND OTHER TOPICAL OR ORAL CANNABINOMIMETIC OR ALIAMIDE MAST CELL INHIBITORS TO TREAT DERMATOHELIOSIS, SEBORRHEIC KERATOSES, AND ANDROGENETIC ALOPECIA

(71) Applicant: William Robert McDaniel, Franklin, TN (US)

(72) Inventor: William Robert McDaniel, Franklin, TN (US)

( * ) Notice: Subject to any disclaimer, the term of this patent is extended or adjusted under 35 U.S.C. 154(b) by 31 days.

(21) Appl. No.: 15/466,821

(22) Filed: Mar. 22, 2017

(65) Prior Publication Data

US 2018/0271761 A1  Sep. 27, 2018

(51) Int. Cl.

| | |
|---|---|
| *A61K 8/02* | (2006.01) |
| *A61K 8/04* | (2006.01) |
| *A61K 8/06* | (2006.01) |
| *A61K 8/42* | (2006.01) |
| *A61Q 5/02* | (2006.01) |
| *A61Q 19/00* | (2006.01) |
| *A61Q 19/08* | (2006.01) |

(52) U.S. Cl.
CPC .............. *A61K 8/42* (2013.01); *A61K 8/0233* (2013.01); *A61K 8/042* (2013.01); *A61K 8/06* (2013.01); *A61Q 5/02* (2013.01); *A61Q 19/00* (2013.01); *A61Q 19/08* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 2003/0049220 A1* | 3/2003 | Bailey | A61K 8/34 424/70.1 |
| 2015/0057269 A1* | 2/2015 | Della Valle | A61K 45/06 514/228.8 |

* cited by examiner

*Primary Examiner* — Kortney L. Klinkel

(57) ABSTRACT

A method of correcting the visible and microscopic signs of Dermatoheliosis (chronic ultraviolet light-damaged human skin) and its various clinical manifestations (wrinkling, sagging, fragility, melasma, Poikiloderma of Civatte, solar lentigines, and senile purpura) and also Androgenetic Alopecia and Seborrheic Keratoses consists of the administration of fatty acid derivatives capable of inhibiting mast cells and the mediators they release that cause local tissue damage. These fatty acid derivatives include palmitoylethanolamide (PEA) and related cannabinomimetic compounds and adelmidrol and related Autacoid Local Injury Antagonist amides (ALIAmides) which are administered orally or applied topically. Adelmidrol, the best absorbed topically, is applied in a concentration of between 1% and 10% by volume, with a preferred concentration of about 5% by volume. Normally produced in body tissues in response to the effects of painful and inflammatory mast cell mediators, these compounds must be added in these conditions to stop the progression of damage because the affected tissues lack inflammation due to the immunosuppressive effects of the chronic ultraviolet radiation that initiates and likely perpetuates them.

17 Claims, No Drawings

USE OF ADELMIDROL AND OTHER TOPICAL OR ORAL CANNABINOMIMETIC OR ALIAMIDE MAST CELL INHIBITORS TO TREAT DERMATOHELIOSIS, SEBORRHEIC KERATOSES, AND ANDROGENETIC ALOPECIA

This invention relates to the treatment of skin conditions traditionally considered not to have inflammation and its accompanying signs of pain, itch, or redness in their pathogenesis, namely chronic sun damage (dermatoheliosis) and its various visible manifestations, seborrheic keratoses, and androgenetic alopecia, with use of topical and oral cannabinomimetic inhibitors of mast cell activity including adelmidrol.

The visible changes exhibited by human skin chronically exposed without screening protection to ultraviolet light in the damaging wavelengths between 290 and 400 nanometers include wrinkling, sagging, thinning, fragility to trauma, easy bruisability, splotchy hyperpigmentation, and an increased tendency for development of malignant, pre-malignant, and benign growths including basal cell and squamous cell carcinomas, melanomas, and actinic and seborrheic keratoses. These end-stage changes, seen with greatly-increased frequency in fair-skinned individuals, have been grouped under the term "dermatoheliosis" to reflect their known cause being ultraviolet light ("helios") exposure. Lavker et al. in a 1988 article were the first to make an in-depth study of the evolution of the process by studying the histology of skin biopsies taken from ultraviolet (UV)-exposed and unexposed skin from 24 patients varying in age from 20 to 80.[1] They focused on changes in the dermis specifically and coined a term "chronic heliodermatitis" to describe the process they noted in the dermal connective tissue environment and its progression without accompanying clinical signs of inflammation. They observed that the earliest sign of the process was increased new elastic fiber production in the younger patients with evolution to massive collections in the dermis of acellular, abnormal elastic tissue and diminished, tortuous vasculature in late stages. They noted a constant presence of mast cells in the tissue in all stages and suggested that they might play a role in the damage. No such increase in mast cell numbers above normal was found in unexposed skin regardless of the age of the patient.

1. Lavker, R M PhD, et al., "Chronic Heliodermatitis: A Morphologic Evaluation of Chronic Actinic Dermal Damage With Emphasis on the Role of Mast Cells", J. Invest. Dermatol., Vol. 90, pp. 325-330, 1988.

The process of dermatoheliosis appears to be unique to the progressive deterioration of normal skin architecture that develops from chronic exposure to the damaging wavelengths of UV light that penetrate into the level of the dermis and its connective tissue and blood vessels specifically. Mast cells, first describes by Ehrlich in 1878, have traditionally been assigned a role in IgE-mediated allergic processes such as asthma, dermatitis, and allergic rhinitis through release of their mediators such as histamine and chemotactic factors that attract inflammatory cells. In tissue reactions to trauma or infections, mast cells are recruited and release mediators that cause pain, itching, redness, and swelling and activate other cells to initiate the healing process. Prior to their recruitment into tissue, they exist in bone marrow and blood as CD34+ lymphocytes. Factors including Stem Cell Factor (SCF) that are released by damaged blood vessels in areas of injury recruit the cells and cause them to transform into tissue mast cells. In tissue, these cells release a barrage of pre-formed mediators and begin the synthesis of new ones under the influence of local cells such as macrophages. Mediators such as Fibroblast Growth Factor (FGF), chymase, and tryptase degrade local tissue constituents and stimulate local fibroblasts and macrophages into increased activity. Nerve Growth Factor (NGF) release causes the pain and itching that typifies local inflammation. It is not the intent of this inventor to enumerate and describe all of the mediators, cytokines, and growth factors known to be produced by tissue mast cells in this description but rather to point out that their armamentarium is entirely sufficient to cause the damage seen in the dermis and epidermis of skin chronically-exposed to damaging UV radiation. Once an initial UV insult triggers the recruitment of mast cells into the perivascular environment of the dermal connective tissue, the normal body processes that inhibit and turn off their destructive activity after infections, trauma, or other inflammatory processes apparently cannot be activated. As will be presented below, this inventor maintains that at least two possible explanations for this inability of the local tissue to turn off the chronic, self-perpetuating mast cell damage are plausible. The first likely factor at play is the known effect of chronic UV radiation in depleting thymus-derived T-lymphocytes in exposed skin, thus depleting the beneficial healing and tissue-protective effects these cells provide in the human body. A second factor could be that some individuals on a hereditary basis lack the ability to produce the local factors including the fatty acid amides and cannabinomimetic compounds of this patent that would normally inhibit the release (degranulation) of mediators from mast cells and reduce their number in tissue. The subclinical degree of the local inflammatory infiltrate in the UV-damaged dermis, which at most should be labeled microinflammation, has prevented the process leading to the various clinical manifestations of dermatoheliosis from being recognized as parts of a process whose initiation as well as its perpetuation is due to the ubiquitous resident tissue mast cells in affected skin, cells uninhibited by the well described tissue mechanisms that deactivate them following overt inflammation. The instant art proposes the use of compounds known either as cannabinomimetics or ALI-Amides (Autacoid Local Injury Antagonist Amides), naturally produced by tissues of the body to limit inflammation and damage by mast cells and available as oral or topical therapeutic agents, to inhibit the destructive changes of mast cells in UV-damaged skin. The desired result of such treatment would be to stop further deterioration and even allow the likely regeneration of normal collagen and elastic tissue, repair of vascular and basement membrane damage, normalization of dyspigmentation and wrinkling, lessening of fragility and bruisability, and prevention of the development of benign, pre-malignant, and malignant skin growths. A case will be made for the likely mast cell role in the progression of Androgenetic Alopecia (AGA), the cause of pattern baldness in men and women, and even for the likely role of UV exposure in its pathophysiology. A series of Examples to follow will expound on the likely role of the mast cell in the various clinical manifestations of dermatoheliosis, seborrheic keratosis, and AGA.

EXAMPLE 1

Melasma, which is translated literally as "black mask", is a disfiguring and distressing splotchy hyperpigmentation of facial skin and less frequently the skin of the neck and forearms. Its incidence in women is far greater than that in men. It has long been recognized to occur with greater frequency in women who are pregnant, who take oral contraceptive medications, or who are experiencing menopause. An increased in local photosensitivity during these times in life may be attributable to a known increase in circulating levels of coproporphyrin, a breakdown product of heme synthesis, during these periods of hormonal alteration. The majority of women who experience it see it resolve after 1-2 years from onset, but at least 20 percent continue to suffer its chronic disfigurement and the resultant significant psychosocial distress. Affected patients must observe near total avoidance of UV exposure or else have increased darkening of affected areas and more obvious contrasting with normally-pigmented skin. While many topical compounds have been developed to lighten the darker pigment, the only consistently effective agent has been hydroquinone. This chemical, which is in use globally, acts by inhibiting the tyrosinase enzyme which is required for the initial stage of pigment production. Toxicity due to its absorption at the high concentrations that are most effective has limited its safe use.

Histologically, skin with melasma contains epidermal melanocytes that are normal in number but have increased melanosomes (pigment-producing cytoplasmic organelles) and increased branching between the epidermal keratinocytes of the basal layer. Marked collagen degeneration and formation of abnormal, fragmented elastic fibers are invariably-present features, seen in striking contrast to adjacent, normally-pigmented skin areas in the same patient, skin which has received the exactly same amount of UV exposure. Blood vessels show laminar thickening of their basement membrane below the endothelial lining and a sparse infiltrate of mononuclear cells around them. The epidermal basal lamina shows perforations and extension of basal keratinocytes into the dermis. Melanophages in the upper dermis contain extravasated epidermal melanin. There is an omnipresent increased population of toluidine blue-positive mast cells in the dermis from the subepidermal area of melanophages to the mid-dermal zone of abnormal elastic fibers and the perivenular region. Clinically, melasma has been described as epidermal or dermal in localization, but evidence points to its being one process that can be in both areas due to the mast cell damage to the basal lamina.

According to the instant art, once mast cells are recruited to the affected tissue by the initial UV damage, either the depleted resident population of beneficial thymus-derived lymphocytes (T cells) in the areas or a genetic inability to produce local mast cell inhibitory compounds allows a perpetual state of local injury in an environment of clinically-undetectable microinflammation. When a sufficient concentration of an ALIAmide or cannabinomimetic mast cell inhibitor is delivered orally or topically to the affected skin, the locally increased pigment in melasma skin will lighten toward normal in the same way that hyperpigmentation following a skin injury or burn fades away over time due to the normal inhibitory processes that turn off the mast cell activity.

EXAMPLE 2

Solar lentigines, or sun-induced freckles, are enlarging macular (flat) hyperpigmented or rarely hypopigmented lesions found exclusively in areas of skin that has undergone chronic UV damage and, as would be expected, more commonly experienced by light-skinned older individuals. Whereas pigmented freckles seen following UV insults in children and adolescents often disappear and never enlarge, solar lentigines increase in diameter with time. Histologically, the dermis below the hyperactive epidermal melanocytes is nearly indistinguishable from that seen in melasma, namely the findings of abnormal elastic tissue, diminished collagen, minimal perivascular mononuclear cell presence, and abundant mast cells. Depleting the number and degranulation of mast cells with delivery of appropriate concentrations of cannabinomimetic or ALIAmide mast cell inhibitors as set forth in this art will result in the reduction or normalization of pigmentation of affected skin lesions. Praetorius et al. studied childhood freckles (ephelides) and solar lentigines and concluded that ephelides represent the direct response of the epidermal melanocytes to acute UV damage in childhood whereas solar lentigines result from the influence on epidermal melanocytes and keratinocytes of fibroblast and mast cell mediators from the underlying dermis.[2]

2. Praetorius, C, et al., "Sun-induced freckling: ephelides and solar lentigines". Pigment Cell Melanoma Research, Vol. 27, pp. 339-350, 2014.

EXAMPLE 3

Poikiloderma of Civatte was described by the French dermatologist Achille Civatte in 1923. The term "poikiloderma" describes the clinical constellation of visible features of the condition including atrophy (thinning), hyperpigmentation, hypopigmentation, and telangiectasias (tiny surface capillaries) seen together in patches on the neck and mandibular area of affected individuals. There is a characteristic sparing of the skin immediately beneath the chin, an area sheltered from UV exposure. The condition is typically seen in light-skinned adults following years of excessive UV exposure. Histologically, Poikiloderma of Civatte was shown by Katoulis et al. to show epidermal atrophy and hyperkeratosis, basal lamina degeneration, increased epidermal melanin, dermal melanophages, and invariable solar elastosis (abnormal elastic fibers).[3] Blood vessels were dilated and were surrounded by a sparse lymphohistiocytic cellular infiltrate. They reported that toluidine blue-staining cells were increased. While they called these cells plasmacytes, toluidine blue is a known mast cell stain because it stains heparin-containing granules which are contained in mast cells but not plasma cells. This histology is identical to that seen in melasma, giving this inventor sufficient reason to consider both conditions to be variable clinical presentations of the same process, one in which the result of chronic UV damage and its suppressive effects on the body's normal immune and reparative processes to allow mast cells to function in an uncontrolled and perpetual damaging fashion. The instant art sets forth as treatment of Poikiloderma of Civatte as in melasma the delivery to the affected tissue of effective mast cell inhibitory concentrations of cannabinomimetic or ALIAmide mast cell inhibitory compounds, the desired result being decreased mast cell mediator damage and normalization of clinical signs due to the return to normal function of the body's repair and healing processes.

3. Katoulis, A C et al., "Poikiloderma of Civatte: a histopathological and ultra-structural study". Dermatology, Vol. 214 (2), pp. 177-182, 2007.

EXAMPLE 4

Easy bruisability is an almost invariable tendency in skin chronically exposed to harmful UV radiation, and is most common and bothersome in skin over the dorsal forearms and hands. The condition has been given the name of senile purpura due to its increased prevalence with aging. One synonym for senile purpura is Bateman's purpura, named after the physician who first described its relationship to chronic UV damage. The aforementioned histopathologic changes described by Lavker et al in dermatoheliosis (or chronic heliodermatitis) are invariably present in skin biopsies of the spreading purple splotches of extravasated red blood cells in the dermis that give rise to the characteristic lesions of senile purpura. Severe alteration of elastic fibers and diminished collagen fibers parallel the diminution in number of normal capillaries and venules. A scant lympho-histiocytic cell infiltrate, increased tissue mast cells, and evidence of damage to dermal blood vessels are typical findings. Borroni et al. studied lesions of Bateman's purpura and adjacent UV-exposed skin and found a statistically-significant thickening of the basal lamina around vessels when compared with skin from young individuals.[4] This thickening reflects the chronic damage to the connective tissue in the basal lamina by mast cell proteases. Also, it is the opinion of this inventor that the release of preformed heparin granules from the mast cells into the perivascular environment causes an inhibition of normal clotting factors and enables greater spread of red blood cells and larger ecchymoses (bruises). Therefore, it logically follows that the instant art involving the delivery of effective concentrations of oral or topical cannabinomimetic or ALIAmide mast cell inhibitors to turn off the deleterious actions of mast cell mediators will result in clinical as well as functional and cosmetic improvement.

4. Borroni, R. et al., "Immunohistochemical study of dermal microvasculature density and vessel basement membrane thickness in Bateman's senile purpura", J. Invest. Dermatol., Vol. 132, pp. 7-13, 2012.

EXAMPLE 5

Seborrheic keratoses are benign tumors of mature skin that are characterized by hyperpigmented buildups of proliferating epidermal keratinocytes with no dermal component at all. The longstanding opinion of experts that the lesions have no connection to UV damage now needs to be corrected. In a study of experimentally-induced chronic UV damage in shaved mouse skin, Saeed et al. were able to induce clinical and histologic seborrheic keratoses in animals exposed to UV but not in animals pretreated with UV-protecting antioxidants before exposure.[5] The evoked tumors exhibited classic features of seborrheic keratosis including pseudo horn cysts and squamous eddies. In the dermis below the lesions were invariably found an increased number of mast cells in the vicinity of blood vessels. Gandi et al., in a study if the mast cell profile of skin lesions, studied malignant skin tumors, seborrheic keratoses, and chronic dermatitis with epidermal hyperplasia and found that while basal cell carcinomas, melanomas, and epidermal hyperplasias showed statistically significant increases in the number of dermal mast cells, the highest number found was beneath seborrheic keratoses (314 per high-power field compared to 39 per high-power field in normal skin).[6] Interestingly, squamous cell carcinoma, which presents with redness, swelling, and pain, showed a reduced number of mast cells, likely due to the body's local production of mast cell inhibitory compounds in response to overt inflammation. In seborrheic keratoses, mast cells were located around superficial dermal blood vessels beneath the proliferative epidermis. Certainly the proliferative changes in the epidermis that cause the hyperpigmentation and hyperplasia can be reduced or reversed by removing the mast cell influences on keratinocytes and melanocytes through the therapeutic use of cannabinomimetic and ALIAmide mast cell inhibitors.

5. Saeed et al., "Epidermal growth factor expression in mice upon ultraviolet B exposure—Seborrheic Keratosis as a coincidental and unique finding", Adv. Biomed. Research, Vol. 1, p. 59, 2012.
6. Gandi, D V et al., "Mast Cell profile in Skin lesions", Int. J. Pharma Res Health Sci, Vol 4 (4), pp. 1280-1283, 2016.

EXAMPLE 6

Androgenetic alopecia (AGA) is a progressive, patterned loss of terminal anagen hair growth affecting the scalp of 55-60% of men and 15% of women. Women often are delayed in onset of the process until natural or surgical menopause when the protective effect of estrogen hormones is lost. It is universally accepted that the condition is promoted by androgen hormones, specifically testosterone and its super-potent derivative dihydrotestosterone (DHT). DHT is produced from testosterone by the action of 5-alpha reductase, the enzyme targeted and inhibited by finasteride, the most effective compound developed for treatment of AGA to date. Because finasteride only gives clinical improvement in roughly 50-60 percent of treated AGA patients, there are obviously other factors at play. This inventor, in a previous US utility patent (U.S. Pat. No. 8,067,470B2), showed that inflammatory porphyrins produced by *Propionibacterium acnes* bacteria that thrive in a reduced linoleic acid scalp oil environment trigger microinflammation and eventual fibrosis and loss of anagen follicles in the affected scalp.[7] Topical linoleic acid application resulted in improved hair growth, especially in subjects who had already been taking finasteride. Histologic studies of AGA have routinely demonstrated sparse inflammation in the perifollicular dermis, fitting the term microinflammation. Clinically, AGA never presents with overt signs of inflammation such as pain, itching, or redness. Still, the perifollicular area of the dermis has a constant presence of mast cells, increased in number above non-AGA scalp areas. Won et al. published results of their study of biopsies from bald and normal areas of scalp of AGA patients and from non-AGA subjects.[8] They found a significant increase in collagen bundles in bald scalp versus non-bald scalp in AGA patients and a four-fold increase in elastic fibers in AGA scalp versus normal control patients. They attributed these changes and the resultant scarring to the two-fold increase in mast cells they found in bald AGA scalp. A known mast cell mediator is Prostaglandin D2 (PGD2). Studies have shown that PGD2 inhibits the hair follicle from entering the anagen phase of hair growth, which is the phase where full-sized terminal hairs are produced. Garza et al. demonstrated that PGD2 applied to the skin of mice stopped hair growth.[9] They also found an elevated level of PGD2 in tissue samples from the bald scalp of men with AGA. Additionally, Larson et al. examined the prostaglandin D synthase enzyme activity of dermal mast cells and found the highest proportion of cells positive in the scalp vertex with a decreasing proportion as samples were tested toward the lateral scalp.[10] This showed a pattern that paralleled the clinical area of AGA. They concluded that this showed an area vulnerable to AGA when other factors triggered it. AGA has been considered by some authors to be photo-aggravated and might in some part be permitted to progress by the effects of chronic UV damage in depleting the body's cellular defense and its anti-inflammatory mast cell inhibitors.[11] Since mast cells contribute to perifollicular fibrosis and produce PGD2, the known inhibitor of anagen hair growth, chemical inhibition of mast cells and their deleterious mediators' actions by the use of cannabinomimetic or ALIAmide mast cell inhibitors as set forth in the instant art will at the very least enhance the effects of known AGA treatments such as finasteride and may provide new stand-alone therapies for affected patients.

7. McDaniel, W R, "Linoleic Acid Preparations For the Topical Treatment of Male and Female Pattern Androgenetic Alopecia, Age-Related Alopecia, and Keratosis Pilaris", U.S. Pat. No. 8,067,470 B2, Issued Nov. 29, 2011
8. Won, C H et al., "Dermal fibrosis in male pattern hair loss: A suggestive implication of mast cells", Arch Dermatol Research, Vol. 300 (3), pp. 147-152, 2008.
9. Garza, L A et al., "Prostaglandin D2 Inhibits Hair Growth and is Elevated in Bald Scalp of Men with Androgenetic Alopecia", Sci Transl Med, 4 (126): 126ra34, 2012.
10. Larson, A R et al., "A prostaglandin D synthase-positive mast cell gradient characterizes scalp patterning", J Cutan Pathol, Vol. 41 (4), pp. 364-369, 2014
11. Trueb, R M et al. "Is Androgenetic Alopecia a Photoagravated Dermatosis?", Dermatology, Vol. 207, pp. 343-348, 2003.

Mast cells were recognized for the toluidine blue dye staining of their sulfated heparin-containing granules by Ehrlich in his doctoral thesis in 1878. As mentioned above, prior to their recruitment into tissue sites of injury, infection, or trauma by SCF and other local signaling compounds, they are found as CD34+ lymphocytes in the bone marrow and circulating in blood. Classically, mast cells producing only tryptase (MCT cells) are found in the lung and intestine whereas those producing tryptase and chymase (MCTC cells) are encountered in connective tissue of skin, conjunctiva, and synovial tissues. Tissue stained with toluidine blue dye identifies mast cells because that dye stains cytoplasmic granules in mast cells that contain sulfated molecules like heparin. Mast cell receptors for IgE antibodies to an innumerable array of antigenic compounds have received the greatest amount of research attention for the cell. Mediators such as histamine and other inflammatory cytokines released following activation of the IgE binding receptor on the cell results in serious immediate sensitivity reactions such as urticaria, asthma, or anaphylaxis. Numerous preformed and newly-synthesized mediators of the mast cell have been studied and characterized. Pertinent to this discussion are histamine, fibroblast growth factor (FGF), and Epidermal Growth Factor (EGF) which stimulate epidermal hyperpigmentation in melasma, Poikiloderma of Civatte, solar lentigines, and seborrheic keratoses. Vascular Epithelial Growth Factor (VEGF) causes vascular changes in all conditions caused by chronic UV damage. Proteases and elastases cause damage to the epidermal basement membrane resulting in leakage of epidermal melanin into the dermis where it is taken up by melanophages. Damage to vascular basal laminas contributes to leakage of blood cells in purpuric conditions. Heparin inhibits blood clotting and magnifies minor traumatic events in UV damaged skin, resulting in large unsightly bruises. PGD2 in scalp mast cells is likely one of several important factors along with androgens that cause progressive loss of terminal hairs in AGA.

One of the leading researchers into the tissue effects of mast cells and also into the body's mechanisms of controlling the local pro-inflammatory and damaging effects of the vast array of stored mast cell mediators was the late Dr. Rita Levi-Montalcini. Having received the Nobel prize in 1986 for the discovery of NGF, one of the mast cell mediators responsible for pain after trauma or inflammation, she focused her lab's efforts in the 1990's on compounds produced locally by the body to stop deleterious mast cell activities.[12] In 1993, she and her colleagues discovered that palmitoylethanolamide (PEA), a food component identified in 1957, acts as a local modulator of hyperactive mast cells and is produced by cells in the body for that purpose. They showed that PEA turned off the pro-inflammatory effects of NGF.

12. Hesselink, J M K, "Professor Rita Levi-Montalcini on Nerve Growth Factor, Mast Cells and Palmitoylethanolamide, an Endogenous Anti-Inflammatory and Analgesic Compound", J Pain Relief, Vol. 2 (1), pp. 114-118, 2013.

PEA and its congeners and derivatives were found to have their activity through at least two mechanisms. They were initially shown to reduce inflammation through activation of receptors of the cannabinoid system, traditionally known as CB1 and CB2. These receptors were discovered in experiments studying the anti-inflammatory effects of *Cannabis sativa*. Classically, the CB1 receptor has been found in the central nervous system and mediates the psychosomatic actions of tetrahydrocannabinol (THC) from marijuana and similar compounds. CB2 is most active in peripheral tissues including skin, synovial tissue, the lung, and the intestine and is likely active in chronic, painful, inflammatory conditions involving these tissues. While PEA in high doses can act on the CB2 receptor, some of its actions still occur even when both CB1 and CB2 receptors are blocked experimentally. Dr. Levi-Montalcini and her colleagues elucidated another inflammation-regulating system beside the Endocannabinoid System (ECS), that in which she described such fatty acid-derived anti-inflammatory compounds as "ALIAmides". She named such compounds, including PEA and its congeners and derivatives and adelmidrol, an amphiphilic (lipid-soluble and water-soluble) amide developed for its increased topical penetrability into skin when compared with PEA, as Autacoid Local Injury Antagonist Amides or ALIAmides. Regardless of the mechanism through which these physiologic compounds produced by the body in response to inflammation, pain, infection, or trauma carry out their tissue-protective and healing effects, the fact is that they are safe and effective. Their use in European countries for decades in inflammatory and painful conditions in humans and animals has confirmed their efficacy and safety. They are considered as therapeutic compounds in the regulatory category of "Medical Foods".

Evidence has been presented in this discussion for the invariable presence of mast cells in the chronic degenerative skin conditions seen in humans in areas of chronic UV light exposure that are considered to be at least initiated by it. These conditions fit the histologic pattern described by Lavker et al. as dermatoheliosis or chronic heliodermatitis. AGA and seborrheic keratoses should be added to this group by virtue of the histologic similarities and the entire lack of clinical signs of overt inflammation despite the presence of a large mast cell presence. The instant art proposes that all of these conditions, once triggered by an initial damaging UV insult, persist and progress through a vicious cycle of further damaging insults due to the recruited mast cells and their mediators' damage of blood vessels, collagen, elastic tissue, the epidermal basal lamina, epidermal and hair follicle cells, and fibroblasts. The effect on the process of chronic UV exposure may merely be the elimination from exposed skin of functioning thymus-derived lymphocytes and their beneficial cytokines which would normally cause local overt inflammation that would invoke the body's own natural cannabinoid or ALIAmide compounds to stop the damage. Some individuals may be unable genetically to produce these compounds also.

Heretofore it has not been recognized that the degenerative changes in skin after chronic UV exposure discussed in this application could be limited, stopped, or even reversed in their various forms by the therapeutic use of oral or topical mast cell inhibitors. None of the conditions ever demonstrate signs of overt inflammation such as pain, itching, redness, or swelling and the absence of such signs has allowed the cell causing the local damage, the tissue mast cell, to be considered as merely an innocent bystander. The instant art maintains that treatment of any of the conditions with oral or topical compounds that provide the local skin tissues with an effective concentration of an inhibitor of mast cells and their degranulation will stop further damage and even allow the normal healing processes of the body to restore more normal architecture and function. At no place in the medical literature has it been suggested that mast cell mediators directly cause the degradation or alteration of tissue in these non-inflammatory conditions. The lack of inflammation allows the mast cell to function without the normal inhibitory effects of the body's intrinsic cannabinomimetic or ALIAmide systems. Since the mast cell has never received its proper incrimination as the villain in dermatoheliosis, seborrheic keratoses, and AGA, the art proposed here of employing topical or oral mast cell inhibitors to treat the conditions is also unprecedented and cannot be considered to be obvious based on prior art or publications. This application contains the first comprehensive grouping of the various forms of dermatoheliosis, seborrheic keratosis, and AGA together due to their non-inflammatory or minimally-inflammatory presentation and their causation or aggravation by resident mast cells. The proposed therapeutic use of known, safe, and effective oral and topical fatty acid-derived mast cell inhibitors presents a novel utility of these compounds in relieving the frustrating and visible stigmata of skin damaged by chronic exposure to UV radiation.

The invention claimed is:

1. A method of treating or improving the visible or microscopic signs of chronic dermatoheliosis comprising orally or topically administering a mast cell inhibitor to a subject having chronic dermatoheliosis and wherein the mast cell inhibitor is palmitoylethanolamide (PEA), adelmidrol or another cannabinomimetic Autacoid Local Injury Antagonist Amide (ALIAmide) and wherein the visible or microscopic signs of dermatoheliosis include wrinkling, sagging, thinning, melasma, Poikiloderma of Civatte, solar lentigines, fragility, and senile purpura.

2. The method of claim 1, wherein said mast cell inhibitor is administered topically and is formulated in a concentration between 1% and 10% by volume.

3. The method of claim 2, wherein said mast cell inhibitor is formulated in a concentration of about 5% by volume.

4. The method of claim 1, wherein said mast cell inhibitor is administered topically and is formulated as a cream.

5. The method of claim 1, wherein said mast cell inhibitor is administered topically and is formulated as a lotion.

6. The method of claim 1, wherein said mast cell inhibitor is administered topically and is formulated as an ointment.

7. A method of treating androgenetic alopecia comprising orally or topically administering a mast cell inhibitor to a subject having androgenetic alopecia, wherein the mast cell inhibitor is palmitoylethanolamide (PEA), adelmidrol or another cannabinomimetic Autacoid Local Injury Antagonist Amide (ALIAmide).

8. The method of claim 7, wherein said mast cell inhibitor is administered topically and is formulated in a concentration between 1% and 10% by volume, or by about 5% by volume.

9. The method of claim 7, wherein said mast cell inhibitor is administered topically and is formulated as a spray.

10. The method of claim 7, wherein said mast cell inhibitor is administered topically and is formulated as a shampoo.

11. The method of claim 7, wherein said mast cell inhibitor is administered topically and is formulated as a gel.

12. A method of removing or reducing the size of seborrheic keratosis from human or animal skin comprising orally or topically administering a mast cell inhibitor to human or animal skin affected with seborrheic keratosis, wherein the mast cell inhibitor is palmitoylethanolamide (PEA), adelmidrol or another cannabinomimetic Autacoid Local Injury Antagonist Amide (ALIAmide).

13. The method of claim 12, wherein said mast cell inhibitor is administered topically and is formulated in a concentration between 1% and 10% by volume, or by about 5% by volume.

14. The method of claim 12, wherein said mast cell inhibitor is administered topically and is formulated as a lotion.

15. The method of claim 12, wherein said mast cell inhibitor is administered topically and is formulated as a cream.

16. The method of claim 12, wherein said mast cell inhibitor is administered topically and is formulated as an ointment.

17. The method of claim 12, wherein said mast cell inhibitor is administered topically and is formulated as an adhesive patch for delivery of the mast cell inhibitor directly into the skin in the location to which it is applied.

* * * * *